United States Patent [19]

Lichty

[11] 4,456,005

[45] Jun. 26, 1984

[54] EXTERNAL COMPRESSION BONE FIXATION DEVICE

[76] Inventor: Terry K. Lichty, Suite 105, St. Francis Professional Bldg., Waterloo, Iowa 50702

[21] Appl. No.: 429,027

[22] Filed: Sep. 30, 1982

[51] Int. Cl.³ .......................... A61F 5/04; A61B 17/18
[52] U.S. Cl. .................................. 128/92 A; 128/92 B
[58] Field of Search ................. 128/92 R, 92 A, 92 B, 128/92 BB

[56] References Cited

U.S. PATENT DOCUMENTS

| | | | |
|---|---|---|---|
| 2,489,870 | 11/1949 | Dzus | 128/92 B |
| 2,511,051 | 6/1950 | Dzus | 128/92 B |
| 2,760,488 | 8/1956 | Pierce | 128/92 A |
| 4,059,102 | 11/1977 | Devas | 128/92 B |
| 4,185,624 | 1/1980 | Gentile | 128/92 A |

FOREIGN PATENT DOCUMENTS 1161507  3/1958  France .............................. 128/92 B

OTHER PUBLICATIONS

W. B. Carrell, M.D. and P. M. Girard, M.D., "Removable Internal Fixation in Fractures," Feb. 28, 1931, pp. 670–673, Jour. A.M.A.

Primary Examiner—Ronald L. Frinks
Attorney, Agent, or Firm—James C. Nemmers

[57] ABSTRACT

An improved external compression bone fixation device for use in the treatment of fractures. The device provides compression on a bone fracture until the fracture has healed. By threading a screw with a threaded shank into the far side of the fracture and then threading a second screw into the other portion of the fractured bone and also onto the shank of the first screw, the fracture is drawn together. When healing has been completed, the screws are removed. The entire procedure can be performed from outside the fractured limb, and a second surgical procedure is not necessary to remove the fixation device after healing.

7 Claims, 4 Drawing Figures

EXTERNAL COMPRESSION BONE FIXATION DEVICE

BACKGROUND OF THE INVENTION

With certain types of fractures, especially oblique fractures in the long bone, use of internal and/or external fixation devices is often the preferred procedure. Such devices that are known are of a variety of types, but they all employ a screw or similar fastener which can be introduced into the two bone fragments to pull them together. Some of these devices fail to accomplish a proper joinder of the fragments because the device, even though threaded into both fragments, is incapable of pulling the fragments sufficiently together to assure proper healing. As a result, entry from both sides of the limb may be necessary so that the fastening device will have a solid member against which the pulling forces can be exerted. Devices of this type are illustrated in Dzus U.S. Pat. No. 2,511,051. Use of such devices obviously requires invasion into the tissues on both sides of the limb.

Moreover, since the surgeon is normally working blind, alignment can be a problem in working from both sides of the limb.

In addition, devices of the prior art provide little or no compression on the fracture but merely maintain alignment of the two fractured segments. Such devices also generally require a surgical procedure to remove the device once healing has been completed.

There is, therefore, a need for an external fixation device which will eliminate the problem of alignment, provide improved compression and which also can be used with a minimum of invasion into the surrounding tissue. There is a further need for such a device which can be quickly and easily removed after healing of the bone fragments without the necessity of a second surgical procedure.

SUMMARY OF THE INVENTION

The device of the invention consists of four components, an inner screw, an outer sleeve-screw and a pair of threaded nuts. The inner screw is threaded and has an upper shaft of a narrower diameter which is also threaded. The outer sleeve-screw contains external threads of the same size as the threads on the lower shaft of the inner screw. The outer sleeve-screw is internally bored to a diameter slightly larger than the threads on the upper shaft of the inner screw. The nuts are each threaded to match the threads on the upper shaft of the inner screw. After a hole is drilled into the two segments of the fractured bone, the inner screw is threaded into the far side of the fracture. The outer sleeve-screw is then threaded into the other fragment with the upper shaft of the inner screw extending into the sleeve-screw until the fragments of the factured bone are drawn together. The nuts are then threaded onto the upper shaft of the inner screw to hold the fragments in place. When the facture is healed, the foregoing process is reversed.

DESCRIPTION OF THE PREFERRED EMBODIMENT OF THE INVENTION

Figure 1:
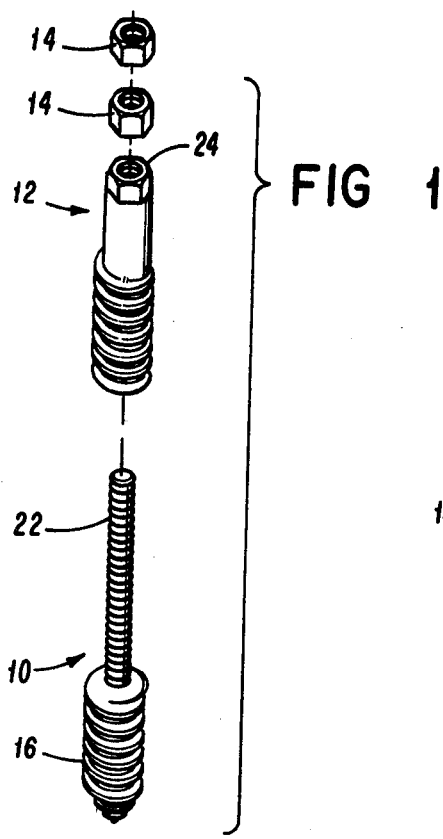
FIG. 1 is an exploded perspective view of the device of the invention.

The device of the invention consists of four components, the distal part 10, a proximal part 12 and two nuts 14.

The distal part 10 has a body 16 that is externally threaded with a thread of the type and size suitable for use in the particular application such as joining two fragments 18 and 20 of a bone. The distal part 10 also includes an upper shaft 22 that is also externally threaded but which has a diameter considerably smaller than that of the body 16. The threads on the upper shaft 22 are of a smaller pitch than the threads on the exterior of the body 16. Also, the threads on the upper shaft 22 can be of any standard machine threads and would be of the same hand as the threads on the body 16.

The proximal part 12 also contains external threads of the same type, size and hand as the external threads on the body 16 of the distal part 10. The proximal part 12 is internally bored from end to end to a diameter that is slightly greater than the external threads on the upper shaft 22. The upper shaft 22 thus serves as a guide for the proximal part 12 and assures that the proximal part 12 and distal part 10 will be precisely aligned. Also, the proximal part 12 has formed integrally with or affixed to it a hex head 24 of a standard size to fit standard size socket or other type wrenches of the hand or power tool types. The interior of hex head 24 is also bored to the same internal diameter as the proximal part 12.

Each nut 14 is preferably of a hexagonal shape to fit standard size socket or other wrenches, and each nut 14 is preferably of the same exterior size as hex head 24. Each nut 14 is internally threaded with threads that match the threads on the upper shaft 22 of the distal part 10.

The actual size of the distal part 10 and proximal part 12 is determined according to the particular application. For example, in repairing bone fractures, the length of the distal part 10 may be approximately 22 millimeters. All components of the device are constructed of any suitable material, preferably a metal alloy such as stainless steel, that is both strong and suitable for internal use without adverse effects to the bone and other tissues.

Figure 2:
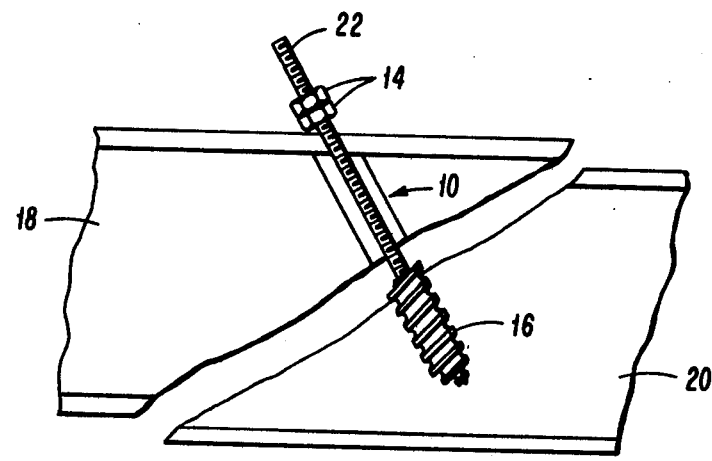
FIG. 2 is a view partly in section and showing the inner screw in place.
Figure 3:
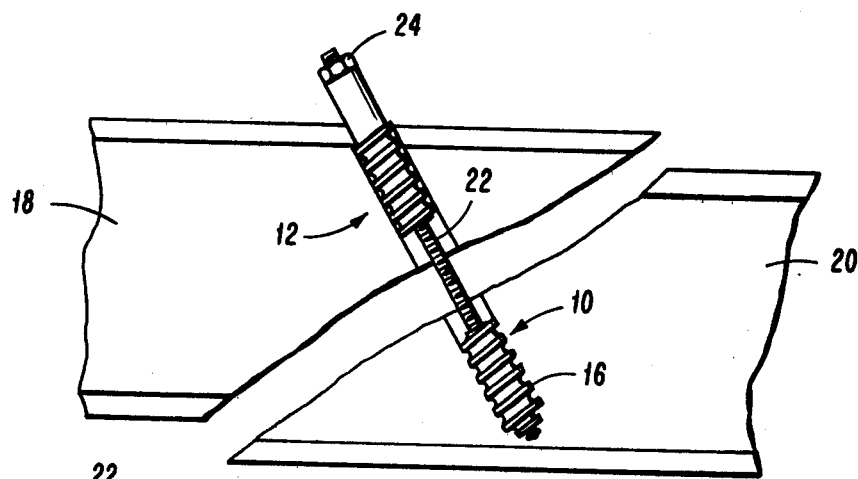
FIG. 3 is a view similar to FIG. 2 and showing the upper sleeve-screw being threaded onto the inner screws.
Figure 4:
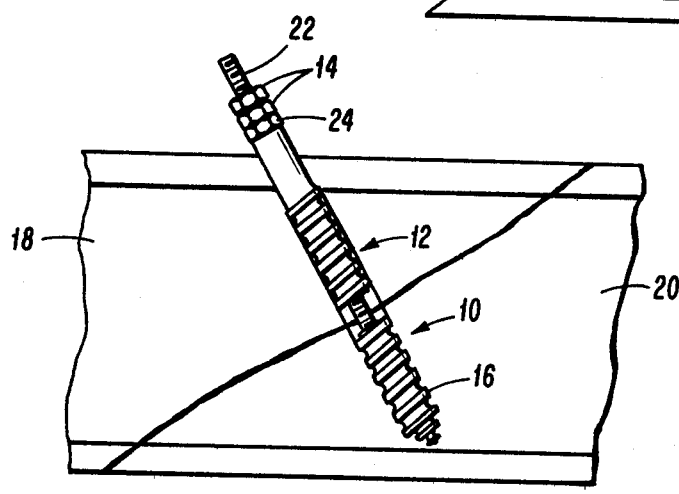
FIG. 4 is a view similar to FIGS. 2 and 3 but showing the device in place with the bone fragments pulled together in proper position for healing.

FIGS. 2, 3 and 4 illustrate the use of the device of the invention. Assuming there is an oblique fracture in one of the long bones of the body or a T-fracture in a joint, the use of a screw type fixation device is generally appropriate. After the fracture has been reduced so that the bone fragments are proximated and are temporarily held in a properly aligned position, a drill is used to bore an opening through the bone fragments which opening is slightly smaller in diameter than the major diameter of the thread on the body 16 of distal part 10. The drill is used to bore an opening through both the proximal fragment 18 and the distal fragment 20 at approximately a right angle to the line of the fracture. Note that the boring occurs from one side of the bone and does not extend completely through to the opposite side. When the boring is completed, two nuts 14 are threaded a slight distance onto the upper shaft 22 of the distal part 10. By use of an appropriate wrench, the distal part 10 is then threaded into the bore opening completely through the proximal fragment 18 and into the distal fragment 20 until the body 16 has passed the fracture line. The two nuts 14 are then removed from the upper shaft 22, and the proximal part 12 is then slid over the upper shaft 22. By applying a suitable wrench to the hex head 24, proximal part 12 is threated into the proximal fragment 18 to a position such as that shown in FIG. 3. A nut 14 is then threaded onto the upper shaft 22 of distal part 10, and by tightening nut 14 with a suitable wrench, the two fragments 18 and 20 will be drawn together until the fragments are properly matched and held securely together as shown in FIG. 4. The first nut 14 is then tightened with a torque wrench until the desired compression is achieved. When this procedure is completed, a second nut 14 may be threaded onto the upper shaft 22 to hold securely the device in place until it is ready to be removed. Both of nuts 14 as well as hex head 24 extend outside of the skin surface, and after completion of the surgical procedure they are properly dressed with a sterile antibiotic dressing.

It will be evident that the device of the invention provides substantial compression of the fractured fragments of the bone whereas many of the prior are devices provide little or no compression but merely maintain alignment of the two fractured bones. This is accomplished by reason of the particular construction in which the distal part 10 has a coarse external thread that engages the bone and also an upper shaft of a smaller diameter which pistons in the proximal part 12 that is engaged in the bone on the opposite side of the fracture. By this technique and construction, each of the two components of the device is securely threaded into the separated fragments of the bone. This provides a forcebase for drawing the two fragments 18 and 20 together as the threaded upper shaft 22 is drawn into the proximal part 12 by tightening nut 14.

When the fracture has completely healed, the device of the invention can be easily removed without the necessity of a second surgical procedure. The foregoing described procedure for insertion of the fixation device is merely reversed. In other words, the nuts 14 are removed, the proximal part 12 is removed, and a double nut 14 is placed on the exposed portion of the upper shaft 22. The double nut 14 is then used to remove the distal part 10.

The device of the invention has several advantages over many prior art external fixation devices. It is technically simpler to use, and it has less hardware exposed above the skin surface, thus minimizing the risk of infection. The device of the invention has wider application than prior art devices to various fractures. There are known advantages of cortical and cancellous bone screws commonly used for internal fixation with compression of bone fractures or osteotomies. The device of the invention has all the advantages of these prior are screws, but its unique aspects provide many additional advantages as well. For example, the device of the invention can be used without creating a "glide hole" for the screws, and it can be applied at any angle without the concern of creating "override" of the fracture or osteotomy. The device of the invention also provides increased thread bearing area in the bone, and since it can be removed without a second surgical procedure, post-healing is greatly improved.

It will be also evident to those skilled in the are that the device of the invention enables the surgeon to create substantial compression on a bone fracture until the bone is healed. This was not possible with most prior art devices.

The invention is intended to incorporate all the advantages of both internal and external fixation devices, and its use eases the task of the surgeon and reduces the expense and morbidity of fracture patients. The device thus is a substantial improvement over prior art devices. Having thus described the invention in connection with a preferred embodiment thereof, it will be further obvious to those skilled in the art that various revisions and modifications can be made to the preferred embodiment without departing from the spirit and scope of the invention. It is my intention, however, that all such revisions and modifications that are obvious to those skilled in the are will be included within the scope of the following claims.

What is claimed is:

1. An external compression bone fixation device for the treatment of bone fractures, said device comprising a distal member having an externally threaded body and a shaft of a smaller diameter than the body, a proximal member having an externally threaded body and an opening extending axially through the body which opening is of a larger diameter than the shaft of the distal member, and means combined with each of the distal and proximal members to provide for turning of said distal and proximal members so that the members can be threaded from one side into the bone on opposite sides of the fracture, said means extending at all times externally of the tissues covering the bone.

2. The device of claim 1 in which the means combined with the proximal member is a portion on the proximal end of the member that is adapted to be engaged by an appropriate hand or power tool.

3. The device of claim 2 in which the shaft of the distal member is threaded, and the means combined with the distal member for turning the member is a pair of removable nuts internally threaded with the same threads as the threads on the shaft.

4. The device of claim 3 in which the threads on the body of the distal member and on the body of the proximal member are coarse threads of the same hand.

5. The device of claims 1, 2, 3 or 4 in which the distal member and proximal member are each made of a material suitable for internal use in the bone.

6. A method of treating bone fractures by use of an external compression fixation device having an externally threaded distal member with an axially extending externally threaded shaft of a samller diameter and an externally threaded proximal member having an opening extending axially through it which opening is of a larger diameter than the diameter of the shaft together with a pair of lock nuts internally threaded to fit the shaft, said method comprising the steps of: drilling through the bone from one side to create an opening on both sides of the fracture which opening is of a diameter slightly smaller than the external diameter of the threads on the distal and proximal members; threading the distal member into the opening until it has crossed the fracture line but not penetrated the surface of the bone on the opposite side; threading the proximal member into the opening with the shaft of the distal member extending through the opening in the proximal member until the proximal member is on the proximal side of the fracture; threading a first nut onto the shaft and tightening the nut until the desired compression is attained; and threading a second nut onto the shaft to hold the components in place.

7. A method of claim 6 in which the distal member is threaded into the opening by threading both nuts onto the shaft and turning the nuts to advance the distal member into the opening.

* * * * *